United States Patent [19]

Yamazaki et al.

[11] Patent Number: 5,449,694
[45] Date of Patent: Sep. 12, 1995

[54] (−)-RITODRINE, THERAPEUTIC COMPOSITIONS AND USE, AND METHOD OF PREPARATION

[75] Inventors: Naoki Yamazaki; Yoshimasa Fukuda; Yoshiaki Shibazaki; Tetsutarou Niizato; Isao Kosugi; Shin Yoshioka, all of Yokohama, Japan

[73] Assignee: Meiji Seika Kabushiki Kaisha, Japan

[21] Appl. No.: 204,160

[22] PCT Filed: Jun. 30, 1993

[86] PCT No.: PCT/JP93/00896

§ 371 Date: Mar. 1, 1994

§ 102(e) Date: Mar. 1, 1994

[87] PCT Pub. No.: WO94/01392

PCT Pub. Date: Jan. 20, 1994

[30] Foreign Application Priority Data

Jul. 1, 1992 [JP] Japan .................................. 4-174087
Aug. 6, 1992 [JP] Japan .................................. 4-210482

[51] Int. Cl.[6] .................... A61K 31/135; C07C 215/60
[52] U.S. Cl. ...................... 514/653; 564/304; 564/364; 564/365
[58] Field of Search ................ 564/304, 364, 365; 514/653

[56] References Cited

U.S. PATENT DOCUMENTS 5,189,219  2/1993  Brussee et al. ...................... 564/356

FOREIGN PATENT DOCUMENTS 0492719  7/1992  European Pat. Off. .

OTHER PUBLICATIONS

Chemical Abstracts, 88(11) col. 69391n (1978).
Chemical Abstracts, 105(3) col. 19181t (1986).
Tetrahedron, 43(6) pp. 1177–1182 (1987).

*Primary Examiner*—Richard L. Raymond
*Attorney, Agent, or Firm*—Wenderoth, Lind & Ponack

[57] ABSTRACT (−)-Ritodrine, that is (−)-erythro-1-(p-hydroxyphenyl)-2-[2-(p-hydroxyphenyl)ethylamino]-1-propanol or a salt thereof substantially free from the (+)-isomer is disclosed. The compound has a strong suppressive effect on uterine contraction in comparison with (±)-ritodrine and (+)-ritodrine and has the same level of toxicity as these compounds, so that it can be used as a therapeutic agent of threatened premature birth and threatened abortion as well as a therapeutic agent of dysmenorrhea having a high safety.

8 Claims, 3 Drawing Sheets

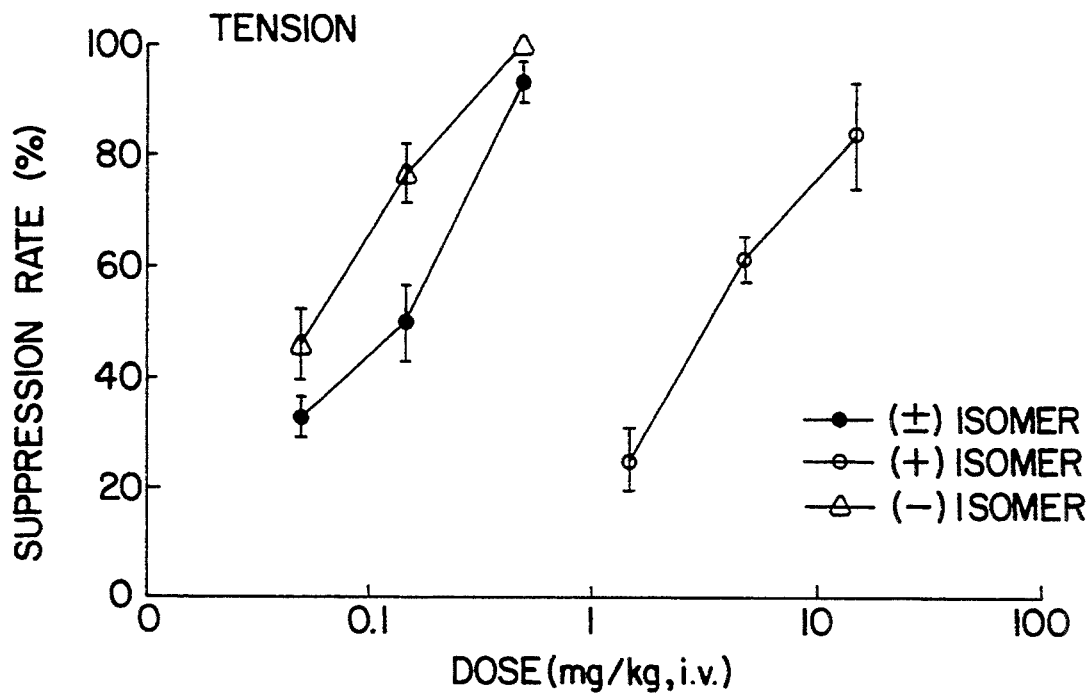
F I G. 2
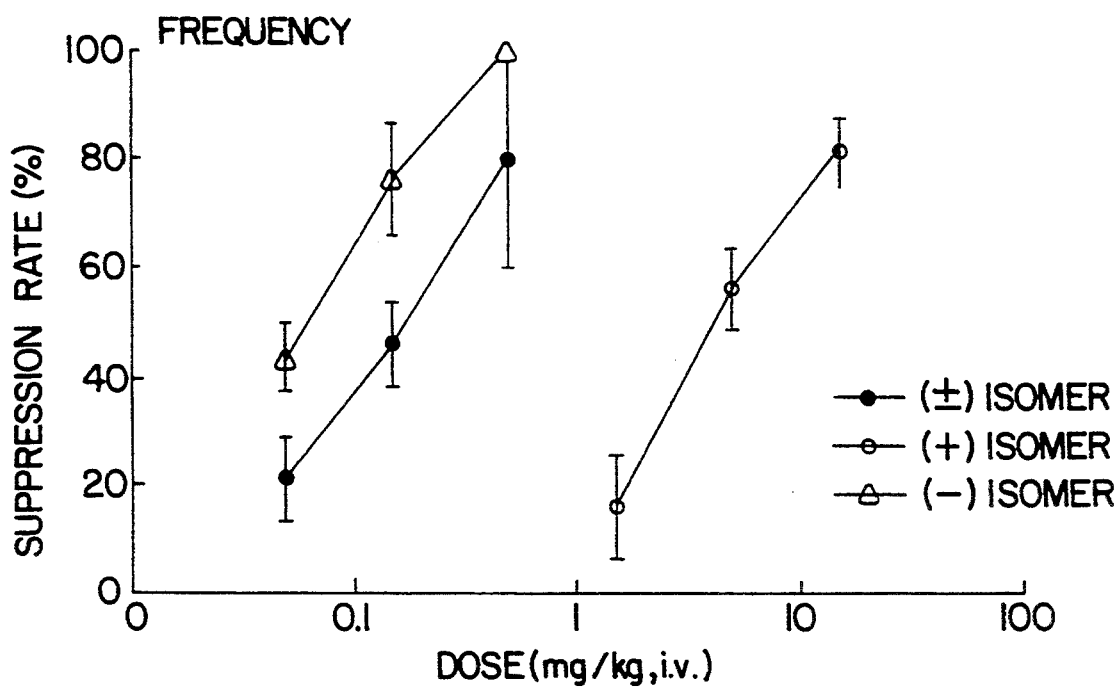
F I G. 3

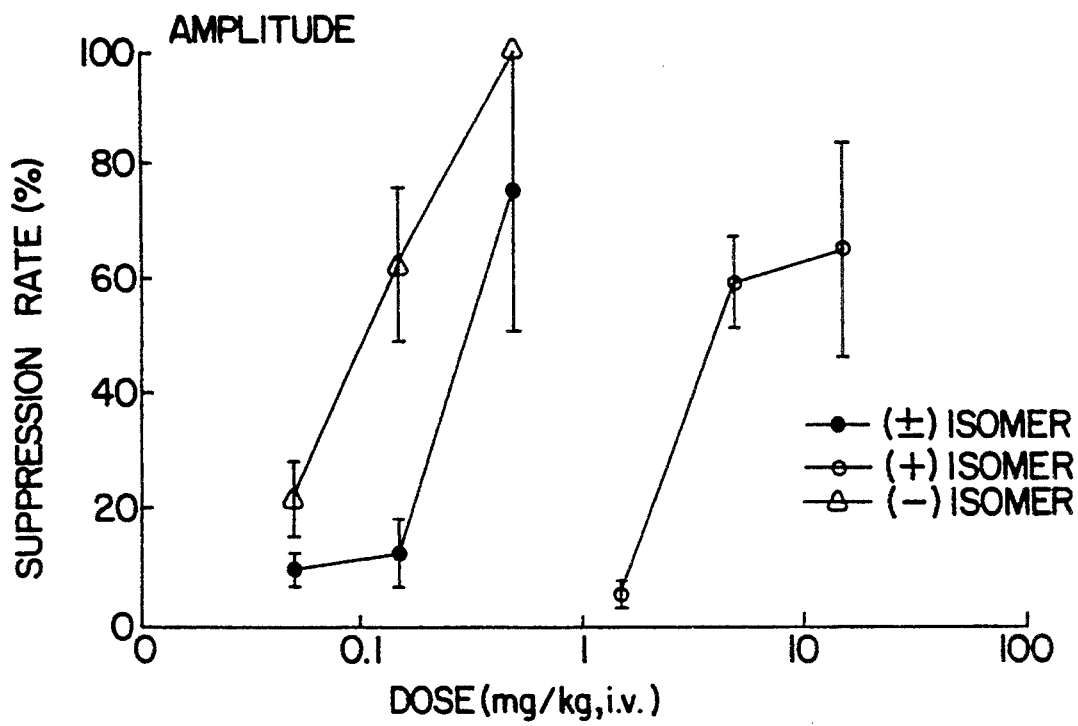
F I G. 4
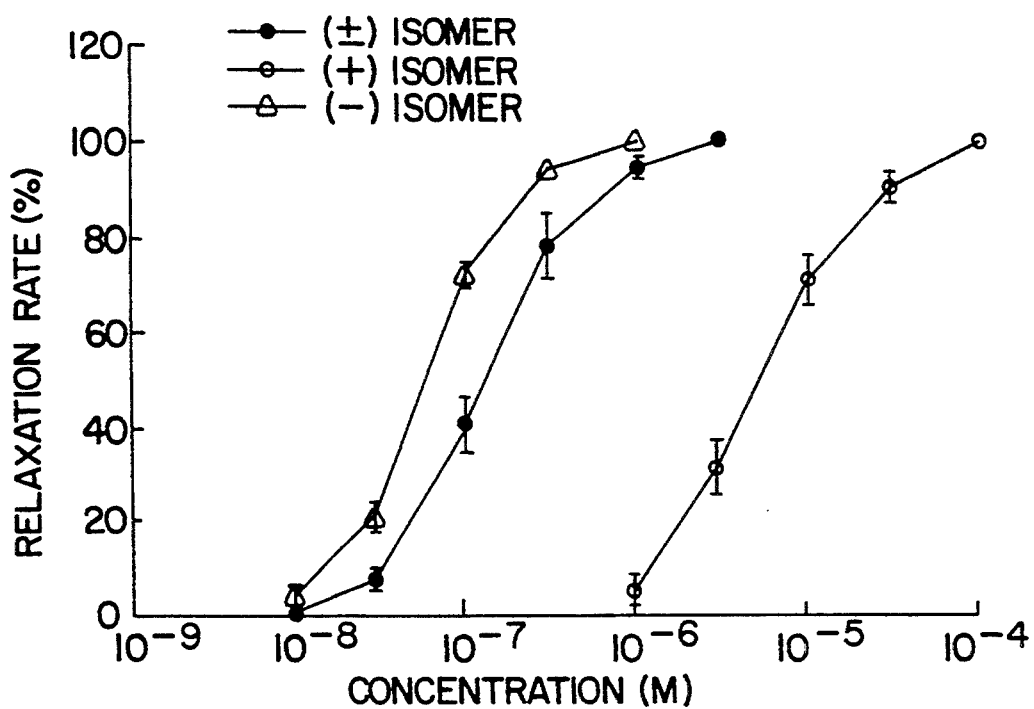
F I G. 5

(−)-RITODRINE, THERAPEUTIC COMPOSITIONS AND USE, AND METHOD OF PREPARATION

This application is a 371 of PCT/JP93/00896, filed Jun. 30, 1993.

BACKGROUND OF THE INVENTION

1. Field of the Art

The present invention relates to a novel optically active ritodrine compound which is effective for the treatment of threatened premature birth and threatened abortion as well as the treatment of dysmenorrhea.

2. Related Art

Ritodrine, (±)-erythro-1-(p-hydroxyphenyl)-2-[2-(p-hydroxyphenyl)ethylamino]-1-propanol, represented by the formula (I):

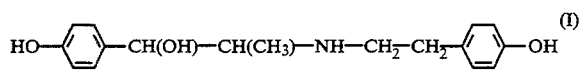

is known to be effective in preventing premature birth owing to its excellent activity for suppressing uterine contraction (Japanese Patent Publication Nos. 10139/1968, 21810/1970 and 22732/1970).

Each of the erythro and threo types of ritodrine structure was anticipated to have two kinds of isomers because of asymmetric carbon atoms at 1- and 2-positions. However, since ritodrine is the racemate of the erythro type ((±)-isomer, specific rotation $[\alpha]_D^{25}=0°$) and the method for obtaining individually the (−)- and (+)-isomers has not been generalized, optically active ritodrines could not be obtained easily.

Therefore, the efficacies or the relationship with side effect of the isomers remained ambiguous and could not be examined. Ritodrines had problems to be solved including the examination of the properties of ritodrine isomers and of their possibilities as medicines, because ritodrines had side effects including an increase in heart rate.

SUMMARY OF THE INVENTION

Therefore, the object of the present invention consists in providing a useful, optically active ritodrine compound which is effective for the treatment of threatened premature birth and threatened abortion as well as the treatment of dysmenorrhea.

The present inventors conducted researches in order to obtain the respective isomers with high purities. It has been described in 10139/1968 that the ritodrine racemate can be resolved into isomers by fractional crystallization, but there is no actual examples in the publication. Furthermore, no reports of successful resolution were described.

The present inventors have also researches on resolving ritodrine by the selective crystallization method or the resolution method by forming various salts, but none of these methods were successful in resolving ritodrine.

However, the present inventors have surprisingly found as a result of examining the optically active column chromatography method that two isomers with such a high purity as no other isomer being detected therein can be obtained by selecting one of many optically active column chromatographies and using a certain solvent system.

The present inventors have also established the method for synthesizing stereoselectively these isomers.

Thus, according to the present invention, pure (−)-ritodrine containing substantially no (+)-ritodrine, that is (−)-erythro-1-(p-hydroxyphenyl)-2-[2-(p-hydroxyphenyl)ethylamino]-1-propanol which is useful for the treatment of threatened premature birth and threatened abortion as well as the treatment of dysmenorrhea or a salt thereof are provided.

Also, according to the present invention, a pharmaceutical composition comprising (−)-ritodrine as an effective component is provided.

Furthermore, according to the present invention, the treatment of threatened premature birth and threatened abortion as well as the treatment of dysmenorrhea comprising administering an effective dose of (−)-ritodrin are provided.

BRIEF DESCRIPTION OF THE DRAWINGS

FIG. 2 is a graph showing the relationship between the dose of (±)-ritodrine, (+)-ritodrine and (−)-ritodrine and the suppression rate (%) of the tension on the oxytocin-induced contraction of uterus in situ;

FIG. 3 is a graph showing the relationship between the dose of (±)-ritodrine, (+)-ritodrine and (−)-ritodrine and the suppression rate (%) of the frequency of spontaneous movement on the oxytocin-induced contraction of uterus in situ;

FIG. 4 is a graph showing the relationship between the dose of (±)-ritodrine, (+)-ritodrine and (−)-ritodrine and the suppression rate of the amplitude of spontaneous movement on the oxytocin-induced contraction of uterus in situ; and FIG. 5 is a graph showing the relationship between the concentration of (±)-ritodrine, (+)-ritodrine and (−)-ritodrine and the relaxation rate (%) of guinea pig tracheal smooth muscle.

DETAILED DESCRIPTION OF THE INVENTION (−)-Ritodrine

Figure 1:
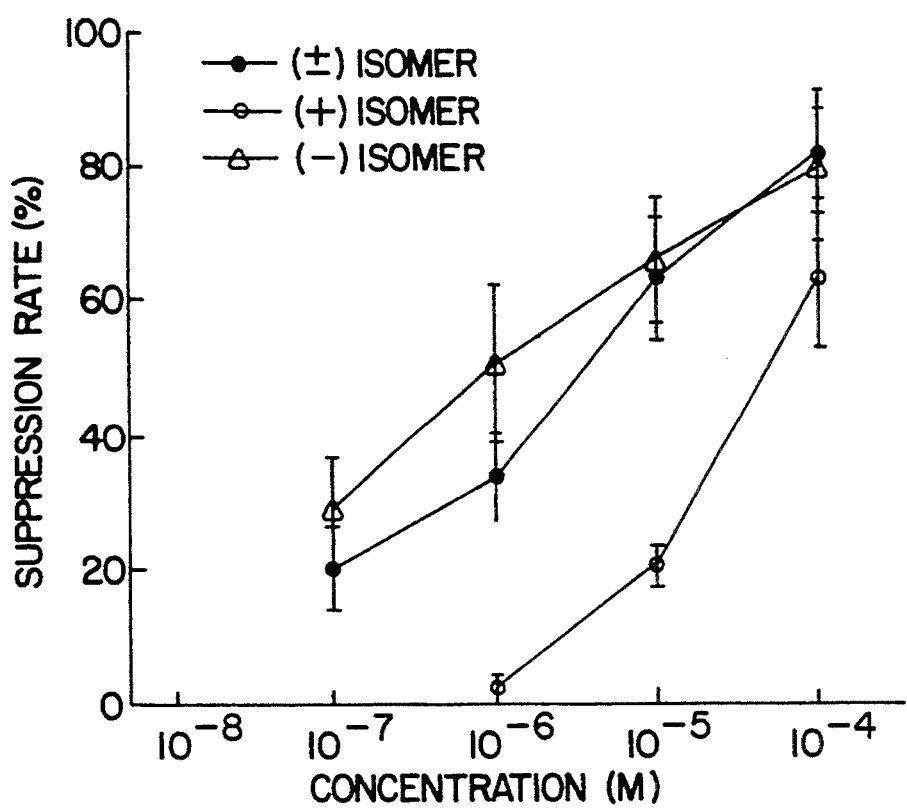
FIG. 1 is a graph showing the relationship between the concentration of (±)-ritodrine, (+)-ritodrine and (−)-ritodrine and the suppression rate (%) on the oxytocin-induced contraction of an isolated rat myometrium.

In this specification, (±)-ritodrine is often referred to as (±)-isomer or merely ritodrine, (−)-ritodrine as (−)-type or (−)-isomer and (+)-ritodrine as (+)-type or (+)-isomer.

(±)-Ritodrine is used for the treatment of threatened premature birth, because it has a relaxation activity on certain smooth muscle due to its $\beta_2$-stimulating effect. The intensity of the activity of (−)-ritodrine is superior to (±)-ritodrine and (+)-ritodrine. Specifically, on comparing the concentrations required for suppressing 50% of the contraction of an isolated myometrium caused by oxytocin (IC$_{50}$), (−)-ritodrine had an intensity of about 2.6 times to that of (±)-ritodrine. On the other hand, (+)-ritodrine had the lowest activity, of which intensity was of 1/15 time to that of (±)-ritodrine.

On comparing the relaxation effects to isolated tracheal muscle via IC$_{50}$, (−)-ritodrine had the highest activity, of which intensity was of about 2.3 times to that of (±)-ritodrine. (+)-Ritodrine has the lowest activity in tracheal muscle, and the intensity was of about 1/40 time to that of (±)-ritodrine.

It is considered from the activities on myometrium and tracheal muscle that the (−)-type has the highest smooth muscle relaxation activity, of which intensity is of 2-3 times to that of the (±)-type. It is also considered that the (+)-type has the lowest smooth muscle relaxation activity, of which intensity is of 1/15-1/40 time to that of the (±)-type.

As for the acute toxicity, all of the (±)-type, (−)-type and (+)-type have a 50% lethal dose ($LD_{50}$) in the range of 50 mg/kg-100 mg/kg.

From the viewpoint of the quantitative ratio of the relaxation activity on smooth muscle and the lethal toxicity, it is believed that safeties in developing the same level of relaxation effect on smooth muscle decrease in the sequence of (−)-type>(±)-type>>(+)-type.

It is considered from the above results that the effectiveness of (−)-ritodrine as a therapeutic of threatened premature birth can be maintained by administering at most the half of the dose of (±)-ritodrine and the toxicity of it can be reduced by half. From these standpoints, (−)-ritodrine can be used as a therapeutic agent of threatened premature birth having few side effects.

(−)-Ritodrine according to the present invention can be separated from (±)-ritodrine by using a specific optical column and a specific solvent system.

Specifically referring to the optically active column and the solvent system, the optically active column includes, for example, DAISEL CHIRAL CELL COLUMN OJ (Daisel Kagaku Kogyo) and DAISEL CHIRAL CELL COLUMN AJ (Daisel Kagaku Kogyo).

The solvent system used in the present invention includes, for example, n-hexane, petroleum ether, ether solvents such as diisopropyl ether and diethyl ether, alcohol solvents such as isopropyl alcohol and ethanol, and if necessary the solvents to which an amine such as diethylamine, triethylamine or the like have been added may be used.

When ritodrine is in the form of a salt, two isomers may also be resolved by high performance liquid column chromatography (HPLC) with an optically active column directly or after having been neutralized into free ritodrine with an organic amine such as triethylamine or an inorganic base such as sodium hydroxide or sodium hydrogen carbonate.

Stereoselective Synthesis of (−)-Ritodrine (−)-Ritodrine according to the present invention can be prepared by reacting the compound represented by the formula (II):

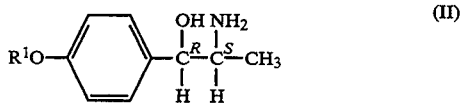

wherein $R^1$ represents an appropriate protective group such as benzyl, methoxymethyl, methoxyethyl or methyl or a group which are not affected by the reaction, with the compound represented by the formula (III):

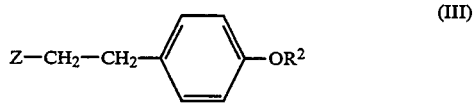

wherein $R^2$ represents an appropriate protective group such as benzyl, methoxymethyl, methoxyethyl or methyl and Z represents a halogen atom or an appropriate removing group such as benzenesulfonyloxy or toluenesulfonyloxy, in an inert solvent such as ethyl ether, tetrahydrofuran or dimethylformamide in the presence of an appropriate base such as triethylamine or sodium methoxide at a reaction temperature of 0°-120° C. (preferably 15°-80° C.) for 124 hours (generally 3-18 hours), if necessary removing the protective groups and optionally converting
the product into a salt such as the hydrochloride. The compound of the formula (II) can be synthesized according to the following scheme:

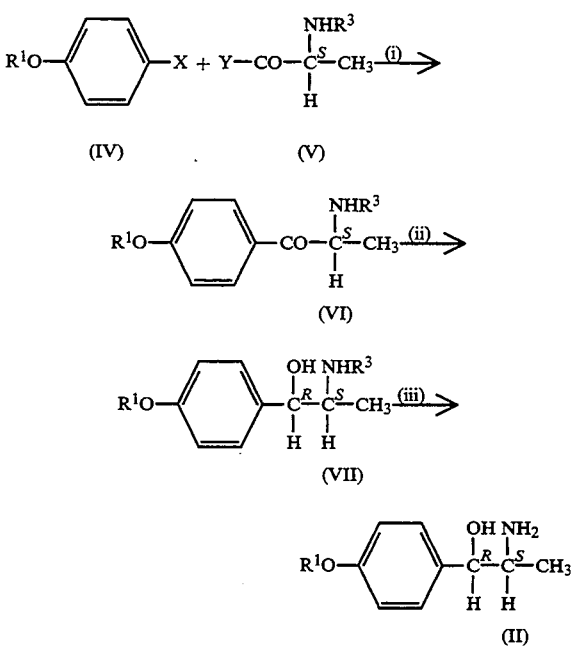

wherein
$R^1$ has the same meanings as defined above,
$R^3$ represents a protective group of an amino group such as ethoxycarbonyl or benzenesulfonyl,
X represents an active metal compound such as —MgBr or lithium, and
Y represents a halogen atom or an alkoxy group such as methoxy or ethoxy.

The step (i) is a modified method of that described by T. F. Buckly III et al. (J. Am. Chem. Soc., 1981, 103, 6157). Briefly, a step for obtaining the optically active compound of the formula (VI) by reacting the compound of the formula (IV) with the compound of the formula (V), an optically active alanine, in an inert solvent such as ethyl ether or tetrahydrofuran at a reaction temperature of −100°-20° C., preferably −70°-0° C. for 1-8 hours, generally 2-6 hours.

The step (ii) is a step for obtaining the optically active compound of the formula (VII) by reacting the compound of the formula (VI) with an appropriate reducing agent such as sodium borohydride, dimethylphenylsilane or potassium selectride in an appropriate solvent such as methanol, ethanol or tetrahydrofuran at a reaction temperature of −80°-20° C. for 1-18 hours, generally 1-4 hours.

Furthermore, the step (iii) is a step for removing the protective group $R^3$ in the compound of the formula (VII). The deprotection may be carried out by heating the compound in aqueous sodium hydroxide-ethanol or by catalytic reduction.

The therapeutic composition for treating threatened premature birth and threatened abortion as well as the treatment of dysmenorrhea may be administered orally or parenterally, for example via intramuscular injection, hypodermic injection or intravenous injection.

When the compound is used as a therapeutic agent of threatened premature birth and threatened abortion, the oral dose, which depends on the conditions of subjects, is generally in the range of 2–10 mg/day. While the parenteral dose is also in the same range as the oral dose, the compound may be administered in a dose of 5–30 mg/day in the case of emergency.

When the compound is used as a therapeutic agent of dysmenorrhea, it is preferably administered in the same dose as that used as the therapeutic agent of threatened premature birth.

As for the pharmaceutical composition, a solubilizing agent for pharmaceutical use may be employed for preparing injections. The compound may be formed into tablets or capsules for oral use with an appropriate carrier.

EXAMPLES

The present invention is now described in detail with reference to the following examples, but it should not be construed that the invention is limited thereto.

EXAMPLE 1

(−)-Erythro-1-(P-Hydroxyphenyl)-2-[2-(P-Hydroxyphenyl)Ethylamino]-1-Propanol Hydrochloride ((−)-Ritodrine Hydrochloride)

To a solution of 1.2 g of (±)-erythro-1-(p-hydroxyphenyl)-2-[2-p-hydroxyphenyl)ethylamino]-1-propanol hydrochloride ((±)-ritodrine hydrochloride) in 12 ml of water was added 311 mg of sodium hydrogen carbonate, and the mixture was left standing for 20 minutes. After 36 ml of ethanol was added, and the insolubles were filtered off and the filtrate was evaporated to dryness. The residue was extracted with 100 ml of ethanol, and the solvent was evaporated. The residue thus obtained was then dissolved in 10 ml of ethanol, filtered with a Millipore filter and concentrated under reduced pressure to give free (±)-ritodrine.

The (±)-ritodrine thus obtained was dissolved in ethanol in a concentration of 50 mg/ml and repeatedly subjected to chromatograph procedure on a DAISEL CHIRAL PACK OJ column (250 mm×20 mm I.D., Lot No. 45-21-20311) with a solvent system of hexane:isopropyl alcohol:diethylamine=70:30:0.1 (V/V/V) at a detection wave length of 278 nm and a flow rate of 10 ml/min at room temperature. The fractions at the retention times of 16 minutes and 23 minutes were collected. The fraction at 23 minutes was concentrated to give (−)-erythro-1-(p-hydroxyphenyl)-2-[2-(p-hydroxyphenyl)ethylamino]-1-propanol ((−)-ritodrine).

The ritodrine thus obtained was converted into (−)-ritodrine hydrochloride by adding hydrochloric acid in an equimolar amount. The analysis of the hydrochloride with a DAISEL CHIRAL PACK OJ column (250 mm×0.46 mm) revealed the content of the (+)-isomer to be 0.1% or less. The (−)-isomer thus obtained had a specific rotation $[\alpha]_D^{25}$ (0.32, ethanol) of −13.7°.

EXAMPLE 2

(a) (S)-2-Ethoxycarbonylamino-1-(4-Methoxyphenyl)-1-Propane

To the ethereal solution (100 ml) of the acid chloride obtained from L-N-ethoxycarbonylalanine (4.98 g) and cooled at −70° C., an ethereal solution (100 ml) obtained from a 4-methoxyphenylmagnesium bromide solution (4-methoxyphenyl bromide (11.575 g)) was slowly dropped over a period of 1 hour. After dropping, the mixture was stirred at −70° C. for 4 hours, and the temperature was slowly raised to −10° C. After the mixture was cooled to −70° C. again, 100 ml of ethyl acetate and 50 ml of water were added. After 10 ml of 5N hydrochloric acid was added, the ethyl acetate layer was separated, dried and concentrated under reduced pressure. The oily material thus obtained was purified by silica gel chromatography (n-hexane-ethyl acetate. (4:1)) to give the title compound (3.84 g) as an oil.

$^1$H NMR (CDCl$_3$) δ 1.25 (3H, t, J=7.2 Hz, CH$_3$), 1.41 (3H, d, J=7.2 Hz, CH$_3$), 3.87 (3H, s, OCH$_3$), 4.13 (2H, q, J=7.2 Hz, CH$_2$), 5.28 (1H, t, J=7.2 Hz, CH), 5.82 (1H, br s, NH), 6.96 (2H, d, J=8.9 Hz, Ar), 7.96 (2H, d, J=8.9 Hz, Ar).

Mass Spectrum, m/z 251 (M+).

(b) (1R,2S)-2-Ethoxycarbonylamino-1-(4-Methoxyphenyl)-1-propanol

To the propanone derivative (4.63 g) obtained in the above step (a) dissolved in 100 ml of methanol, sodium borohydride (1.05 g) was added slowly. After the mixture was stirred for 2 hours at room temperature, 1 ml of acetic acid was added and the resulting mixture was concentrated under reduced pressure. The residue was extracted with ethyl acetate, washed with water, dried and concentrated under reduced pressure. The residue was purified by silica gel chromatography (n-hexane-ethyl acetate (1:1)) to give the title compound (2.28 g) as an oil.

$^1$H NMR (CDCl$_3$) δ 0.95 (3H, d, J=6.6 Hz, CH$_3$), 1.21 (3H, t, J=7.0 Hz, CH$_3$), 3.64 (1H, s, OH), 3.77 (3H, s, OCH$_3$), 3.94 (1H, br m, CH), 4.07 (2H, q, J=7.0 Hz, CH$_2$), 4.78 (1H, s, NH), 5.20 (1H, br d, J=8.1 Hz, CH), 6.84 (2H, d, J=8.6 Hz, Ar), 7.24 (2H, d, J=8.6 Hz, Ar).

Mass Spectrum, m/z 253 (M+).

(c) (1R,2S)-2-Amino-1-(4-Methoxyphenyl)-1-Propanol

The protected amino derivative (1.50 g) obtained in the above step (b) was dissolved in a mixed solution of methanol (30 ml) and an aqueous solution (10 ml) containing 0.6 g of potassium hydroxide. The mixture was heated under reflux for 11 hours, concentrated under reduced pressure, dissolved in ethyl acetate, washed with water and then concentrated. The residue was crystallized with n-hexane to give 893 mg of the title compound.

$^1$H NMR (CDCl$_3$) δ 0.85 (3H, d, J=6.4 Hz, CH$_3$), 2.83 (1H, dq, J=5.2, 6.4 Hz, CH), 3.73 (1H, s, OCH$_3$), 4.23 (1H, d, J=5.2 Hz, CH), 6.86 (2H, d, J=8.7 Hz, Ar), 7.21 (2H, d, J=8.7 Hz, Ar).

Mass Spectrum, m/z 180 (M+).

(d) (1R, 2S)-2-(4-Benzyloxyphenethylamino)-1-(4-Methoxyphenyl)-1-Propanol

To the compound (530 mg) obtained in the above step (c) dissolved in 10 ml of dimethylformamide, 4-benzyloxyphenethyl bromide (940 mg) and potassium carbonate (814 mg) were added. the mixture was reacted at room temperature for 24 hours and further heated at 50° C. for 8 hours. The mixture was extracted with ethyl acetate and water, and the ethyl acetate layer was dried and concentrated under reduced pressure. The residue was purified by silica gel chromatography to give the title compound (380 mg).

$^1$H NMR (CDCl$_3$) δ 0.83 (3H, d, J=6.6 Hz, CH$_3$), 2.74 (2H, m, CH$_2$), 2.86 (2H, m, CH), 2.94 (1H, m, CH), 3.77 (3H, s, OCH$_3$), 4.68 (1H, d, J=3.7 Hz, CH), 5.03 (2H, s, CH$_2$), 6.84 (2H, d, J=8.8 Hz, Ar), 6.89 (2H, d, J=8.8 Hz, Ar), 7.09 (2H, d, J=8.8 Hz, Ar), 7.19 (2H, d, J=8.8 Hz, Ar).

Mass Spectrum, m/z 391 (M+).

(e) (1R,2S)-2-(4-Hydroxyphenethylamino)-1-(4-hydroxyphenyl)-1-propanol hydrochloride ((−)-ritodrine)

The compound (1.03 g) obtained in the above step (d) was dissolved in 30 ml of methylene chloride and cooled to −25° C. and a 1N boron tribromide-methylene chloride solution (8.5 ml) was added. The mixture was reacted at −25° C. for 30 minutes and at −5° C. for 5 hours and then poured into 100 ml of water. After the methylene chloride layer was separated, the aqueous layer was adjusted to a pH value of 6.5. The aqueous solution was adsorbed on a high porous resin HP-20 and eluted with 50% methanol. The combined eluates were concentrated, and the residue was purified by silica gel chromatography using chloroform-methanol (3:1 (V/V)) as an eluent to give the title compound as the free base. After 3 ml of water and 0.6 ml of concentrated hydrochloric acid were added to the free base thus obtained, the mixture was lyophilized to give the hydrochloride (113 mg). The compound thus obtained had the same retention time as (−)-ritodrine in optically active HPLC (CHIRAL PACK OJ, n-hexane-isopropanol-diethylamine (75:25:0.1 (v/v/v)).

$^1$H NMR (CDCl$_3$) δ 0.97 (3H, d, J=7.6 Hz, CH$_3$), 2.92 (2H, m, CH$_2$), 3.14 (2H, br s, CH$_2$), 3.31 (1H, br, CH), 5.09 (1H, s), 5.95 (1H, d, J=4.4 Hz, CH), 6.73 (2H, d, J=8.7 Hz, Ar), 6.76 (2H, d, J=8.7 Hz, Ar), 7.06 (2H, d, J=8.7 Hz, Ar), 7.16 (2H, d, J=8.7 Hz, Ar).

$[α]_D^{20}$ −13.2° (c 0.24, ethanol).

BIOLOGICAL TEST 1

Effect on an Isolated Rat Myometrium Preparation

After blowing the cranium of a female virgin Wistar rat, uterus was extracted. The preparation was suspended in a Magnus tube filled with a nutrient solution (Tyrode solution) which was maintained at 36°±1° C. and saturated with a mixed gas of 95% O$_2$ and 5% CO$_2$. Contractile tension was measured via an isotonic transducer and recorded on a polygraph. When the spontaneous movement was stabilized, oxytocin (2×10$^{-2}$ U/ml) was administered and either (±)-ritodrine hydrochloride, (+)-ritodrine hydrochloride or (−)-ritodrine hydrochloride (10$^{-7}$-10$^{-4}$M) was applied to the Magnus tube to observe the variation of the contractile tension. Suppresive effect on the oxytocin-contracted uterus was expressed by the intensity of activity of (±)-ritodrine hydrochloride, (+)-ritodrine hydrochloride or (−)-ritodrine hydrochloride based on 100% of the contraction by oxytocin.

Results are shown in Table 1. The (±)-isomer and (−)-isomer exhibited relaxation activities even at concentration of 10$^{-7}$M, and the activities increased depending on the concentration. The (+)-isomer exhibited the activity at a concentration of 10$^{-5}$M and more. The concentration required for suppressing 50% of the contraction of an isolated myometrium caused by oxytocin (IC$_{50}$) was 3.53×10$^{-6}$M of (±)-isomer, 1.35×10$^{-6}$M of (−)-isomer and 5.46×10$^{-5}$M of (+)-isomer.

BIOLOGICAL TEST 2

Effect on Uterine Movement in Situ

After a pregnant Wistar rat was anesthesized with urethane-α-chloralose, the abdominal part was incised along the median line and a polyethylene cylinder was inserted. The center of the uterine horn was suspended with a suture, and the uterine movement was isotonically recorded via an isotonic transducer. When the spontaneous movement of the uterus was stabilized, 50 mU/kg/min of oxytocin was infused intravenously to facilitate the movement. When the response due to oxytocin became constant, either (±)-ritodrine hydrochloride, (+)-ritodrine hydrochloride or (−)-ritodrine hydrochloride (0.05-15 mg/kg) was administered intravenously to observe the variation of tension and frequency and amplitude of the spontaneous movement. The suppressing effect of the uterine movement on respective parameters was expressed as the intensity of the activity by either (±)-ritodrine hydrochloride, (+)-ritodrine hydrochloride or (−)-ritodrine hydrochloride based on the state facilitated by oxytocin as 100%. The variations of the tension, and the frequency and amplitude of the spontaneous movement are shown in Tables 2, 3 and 4, respectively. The (±)-isomer and (−)-isomer exhibited suppressing effects at a dose of 0.05 mg/kg or more, and the effects increased depending on the concentration. In either parameter, the (−)-isomer was effective in a concentration of ½-⅓ to the (±)-isomer. The (+)-isomer was effective at a dose of 1.5 mg/kg or more. The concentration required for suppressing 50% of the increased of the uterus due to oxytocin was 0.059 mg/kg for the (−)-isomer, 0.106 mg/kg for the (±)-isomer and 3.61 mg/kg for the (+)-isomer.

BIOLOGICAL TEST 3

Effect on an Isolated Preparation of Tracheal Muscle in Guinea Pig

After Hartley guinea pigs having body weight of 430-510 g, were anesthesized with ether, tracheae were excised to make chain preparation according to the method of Akcasu (A. Akcasu, Arch. Int. Pharmacodyn., 1959, 122, 201). The preparations were suspended in a Magnus tube filled with an air-saturated nutrient solution (Tyrode solution) maintained at 37°±1° C. Contractile tension was measured via an isotonic transducer and recorded on a polygraph. Either (±)-ritodrine hydrochloride, (+)-ritodrine hydrochloride or (−)-ritodrine hydrochloride was cumulatively applied so as the concentration in the Magnus tube to be 10$^{-8}$-10$^{-4}$M.

The results are shown in Table 5. All of the (±)-isomer, the (−)-isomer and the (+)-isomer exerted relaxation response depending on concentration. The intensities of the activity decreased in the sequence of (−)-isomer>(±)-isomer>>(+)-isomer. The concentration required for relaxing 50% of the maximum relaxation effect (IC$_{50}$) was 5.97×10$^{-8}$M for the (−)-isomer, 1.36×10$^{-7}$M for the (±)-isomer and 5.61×10$^{-6}$M for the (+)-isomer.

BIOLOGICAL TEST 4

Acute Toxicity Test in Mouse (±)-Ritodrine hydrochloride, (+)-ritodrine hydrochloride or (−)-ritodrine hydrochloride was administered intravenously at a dose of 40–100 mg/kg to male ICR mice to examine their motality. The results are shown in Table 1.

TABLE 1

| Optically active compound | Acute toxicity test in mice (i.v.) | | | | | | | $LD_{50}$ (Confidence limit) |
|---|---|---|---|---|---|---|---|---|
| | Dose (mg/kg) | | | | | | | |
| | 40 | 50 | 60 | 70 | 80 | 90 | 100 | |
| (−)-isomer | 0/5 | 1/5 | 3/5 | 3/5 | 3/5 | 5/5 | — | 64 (53–76) |
| (±)-isomer | — | 0/5 | 0/5 | 1/5 | 2/5 | 4/5 | 4/5 | 83 (73–95) |
| (+)-isomer | — | 0/5 | 1/5 | 2/5 | 4/5 | 5/5 | — | 70 (62–79) |

BIOLOGICAL TEST 5

Effect on Vascular Permeability

Three Hartley guinea pigs were employed. (±)-Ritodrine hydrochloride, (+)-ritodrine hydrochloride or (−)-ritodrine hydrochloride were administered intracutaneously at a dose of $10^{-2}$–$10^{-5}$ g/ml into the shaved rear part of the guinea pigs. Immediately after the administration, 1 ml of a 1% Evans blue solution was administered intravenously. After 30 minutes, the animals were slaughtered by exsanguination under anesthetization with excessive amount of pentobarbital sodium. The skin was peeled to observe from the internal side of the skin the extent of dye infiltration at the site where the test material was administered. The area with dye having a size ([longer diameter+shorter diameter]/2) of 5 mm or more was judged positive. The results are shown in Table 2.

TABLE 2

| Vascular Permeability test in guinea pig | | | | |
|---|---|---|---|---|
| Optically active compound | Concentration (%) | | | |
| | 0.001 | 0.01 | 0.1 | 1 |
| (−)-isomer | 0/3 | 1/3 | 2/3 | 3/3 |
| (±)-isomer | 0/3 | 0/3 | 3/3 | 3/3 |
| (+)-isomer | 0/3 | 1/3 | 3/3 | — |

What we claim is:

1. (−)-Erythro-1-(p-hydroxyphenyl)-2-[2-(p-hydroxyphenyl)ethylamino]-1-propanol or a salt thereof substantially free from the (+)-isomer.

2. A therapeutic composition for treating threatened premature birth and threatened abortion, comprising the compound claimed in claim 1 as an active ingredient and a pharmaceutically acceptable carrier.

3. A therapeutic composition for treating dysmenorrhea, comprising the compound claimed in claim 1 as an active ingredient and a pharmaceutically acceptable carrier.

4. A process for treating threatened premature birth and threatened abortion, comprising the step of administering the effective amount of the compound claimed in claim 1.

5. A process for treating dysmenorrhea, comprising the step of administering the effective amount of the compound claimed in claim 1.

6. A method for preparing a compound according to claim 1 comprising:

reacting a compound of formula (II):

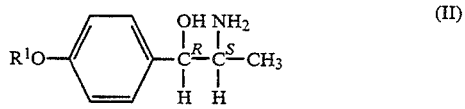

wherein $R^1$ represents a protective group, with the compound of formula (III):

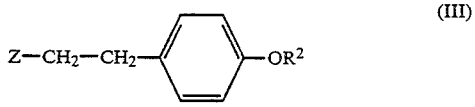

wherein $R^2$ represents a protective group and Z represents a halogen atom or a leaving group, and optionally, deprotecting the resulting compound and/or converting the resulting compound into a pharmaceutically acceptable salt.

7. The method according to claim 6, wherein $R^1$ and $R^2$ independently represent benzyl, methoxymethyl, methoxyethyl or methyl, and Z represents halogen or benzenesulfonyloxy or tolunesulfonyloxy.

8. A method for isolating a compound according to claim 1, comprising:

placing (±)-erythro-1-(p-hydroxyphenyl)-2-[2-(p-hydroxyphenyl)ethylamino]-1-propanol in an optical column, and eluting the column with a solvent system.

* * * * *